US012758111B2

(12) United States Patent
Zhou et al.

(10) Patent No.: US 12,758,111 B2
(45) Date of Patent: Oct. 13, 2026

(54) SIGNAL ACQUISITION DEVICES

(71) Applicant: SHENZHEN SHOKZ CO., LTD., Shenzhen (CN)

(72) Inventors: Xin Zhou, Shenzhen (CN); Yifeng Gan, Shenzhen (CN); Yuxiang Zhang, Shenzhen (CN); Fengyun Liao, Shenzhen (CN); Xin Qi, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 2 days.

(21) Appl. No.: 18/789,654

(22) Filed: Jul. 30, 2024

(65) Prior Publication Data

US 2024/0382099 A1 Nov. 21, 2024

Related U.S. Application Data

(63) Continuation of application No. PCT/CN2022/108315, filed on Jul. 27, 2022.

(51) Int. Cl.
*A61B 5/05* (2021.01)
*A41D 13/12* (2006.01)
*H01Q 1/27* (2006.01)

(52) U.S. Cl.
CPC ................ *A61B 5/05* (2013.01); *A41D 13/12* (2013.01); *H01Q 1/273* (2013.01)

(58) Field of Classification Search
None
See application file for complete search history.

(56) References Cited

U.S. PATENT DOCUMENTS

2007/0038057 A1 2/2007 Nam et al.
2007/0299325 A1 12/2007 Farrell et al.
(Continued)

FOREIGN PATENT DOCUMENTS

CN 208479206 U 2/2019
CN 111920383 A 11/2020
(Continued)

OTHER PUBLICATIONS

International Search Report in PCT/CN2022/108315 mailed on Apr. 25, 2023, 8 pages.
(Continued)

*Primary Examiner* — Michael J Carey
*Assistant Examiner* — Marjan Saboktakin
(74) *Attorney, Agent, or Firm* — METIS IP LLC

(57) ABSTRACT

Embodiments of the present disclosure provide a signal acquisition device including a wearable object provided with a sensor, a sub-base, and a mother base fixed on the wearable object. The wearable object is configured to be worn on a user and acquire a physiological signal of the user via the sensor. The sub-base is configured to accommodate a circuit structure. The circuit structure includes a power supply circuit and a signal transmitter, the power supply circuit is configured to supply power to the sensor, and the signal transmitter is configured to send the physiological signal to an external device. The sub-base is detachably connected with the mother base. The mother base includes a transmission interface. When the mother base is connected with the sub-base, the circuit structure is electrically connected with the sensor via the transmission interface.

20 Claims, 12 Drawing Sheets

(56) References Cited

U.S. PATENT DOCUMENTS

| | | | | |
|---|---|---|---|---|
| 2014/0213878 | A1 | 7/2014 | Banet et al. | |
| 2014/0330090 | A1 | 11/2014 | Banet et al. | |
| 2014/0343391 | A1* | 11/2014 | Korkala | A61B 5/6823 29/832 |
| 2016/0038083 | A1 | 2/2016 | Ding et al. | |
| 2016/0100758 | A1 | 4/2016 | Jeong | |
| 2019/0094088 | A1* | 3/2019 | Reif | A61B 5/6807 |

FOREIGN PATENT DOCUMENTS

| | | | | |
|---|---|---|---|---|
| CN | 112022118 | A | 12/2020 | |
| GB | 2595494 | A * | 12/2021 | A61B 5/6804 |
| KR | 20080021267 | A | 3/2008 | |
| KR | 101346769 | B1 * | 12/2013 | A41D 1/005 |
| RU | 14266 | U1 * | 7/2000 | |
| RU | 142661 | U1 | 6/2014 | |
| RU | 176906 | U1 | 2/2018 | |

OTHER PUBLICATIONS

Written Opinion in PCT/CN2022/108315 mailed on Apr. 25, 2023, 6 pages.

The Extended European Search Report in European Application No. 22952338.6 mailed on Apr. 15, 2025, 12 pages.

* cited by examiner

520

520

SIGNAL ACQUISITION DEVICES

CROSS-REFERENCE TO RELATED APPLICATIONS

This application is a Continuation of International Application No. PCT/CN2022/108315, filed on Jul. 27, 2022, the entire contents of which are incorporated herein by reference.

TECHNICAL FIELD

The present disclosure relates to the field of signal acquisition, and in particular, to a signal acquisition device.

BACKGROUND

Currently, a physiological signal related to real-time physiological state may be obtained through a sensor (e.g., a myoelectric sensor, a temperature sensor, an inertial sensor, or a stress sensor, etc.). For example, relevant physiological parameters of a user while performing an exercise may be obtained by integrating the sensor in a garment, thus the user's physical state may be monitored in real time, and the collected physiological signal may be dynamically analyzed. However, information captured by the sensor needs to be efficiently and stably transmitted to a circuit for further processing and transmitting the signal to ensure the quality of the signal. At this time, the circuit and power supply are also integrated into the garment, making the garment difficult to wash.

Therefore, it is desired to provide a signal acquisition device that is easy to wash and has a high stability during the movement of the user.

SUMMARY

One of the embodiments of the present disclosure provides a signal acquisition device including a wearable object provided with a sensor, a sub-base, and a mother base fixed on the wearable object. The wearable object may be configured to be worn on a user and acquire a physiological signal of the user via the sensor. The sub-base may be configured to accommodate a circuit structure. The circuit structure may include a power supply circuit and a signal transmitter, the power supply circuit may be configured to supply power to the sensor, and the signal transmitter may be configured to send the physiological signal to an external device. The sub-base may be detachably connected with the mother base, and the mother base may include a transmission interface. When the mother base is connected with the sub-base, the circuit structure may be electrically connected with the sensor via the transmission interface.

In some embodiments, the circuit structure may include a transmission plug adapted to the transmission interface. The transmission plug may be electrically connected with the signal transmitter and the power supply circuit. The mother base may be provided with a groove, and at least a portion of the sub-base may be detachably connected with the mother base through the groove. The transmission interface may be located at the groove, and the transmission plug may be s electrically connected with the transmission interface when the sub-base is connected with the mother base.

In some embodiments, the sub-base may include a raised structure adapted to the groove, the raised structure may project outwardly relative to a body of the sub-base, and the transmission plug may be embedded in the raised structure. The transmission plug may be electrically connected with the transmission interface when the raised structure is mated with the groove.

In some embodiments, one of the transmission plug and the transmission interface may include a plurality of pop pins, and the plurality of pop pins may be distributed in an array; the other of the transmission plug and the transmission interface may include a plurality of contact points, and the plurality of contact points may correspond to the plurality of pop pins one by one. When the transmission plug is electrically connected with the transmission interface, the end portions of the plurality of contact points may in contact with end portions of the plurality of pop pins one by one.

In some embodiments, the raised structure may include a recessed portion, the recessed portion may be located at an end of the raised structure away from the body of the sub-base, and the transmission plug may be embedded in a bottom wall of the recessed portion.

In some embodiments, the bottom wall of the recessed portion may be provided with a plurality of first holes, the plurality of first holes may correspond to the plurality of pop pins one by one, and at least a portion of the plurality of pop pins may protrude through the plurality of first holes to an outer side of the sub-base.

In some embodiments, an end of each of the plurality of pop pins in contact with each of the plurality of contact points may be lower than the end of the raised structure away from the body of the sub-base along a protruding direction of the raised structure relative to the sub-base.

In some embodiments, the transmission plug may further include a first adapter board, the first adapter board may be located in the sub-base and cover the bottom wall of the recessed portion, and the plurality of pop pins may be distributed on the first adapter board.

In some embodiments, the circuit structure may further include a first circuit board. The transmission plug may be connected with the power supply circuit and the signal transmitter through the first circuit board, the first circuit board may be connected to a side of the first adapter board back from the plurality of pop pins, the first circuit board may overlap with the first adapter board in a projection plane perpendicular to an insertion direction of the sub-base and the mother base, and the first circuit board may be fixedly connected with the sub-base.

In some embodiments, the circuit structure further may include a flexible circuit board, the first circuit board may include a first snap-on interface, the first adapter board may include a second snap-on interface, and two ends of the flexible circuit board may be electrically connected with the first snap-on interface and the second snap-on interface, respectively, to cause the first circuit board to be electrically connected with the first adapter board.

In some embodiments, the sub-base may further include at least one of an indicator light, a charging port, a data port, and a button, and the sub-base may be provided with at least one second hole for mounting the indicator light, the charging port, the data port, or the button.

In some embodiments, the groove may be provided with a mounting port, the mounting port may be located at a bottom of the groove, and the transmission interface may be embedded in the groove through the mounting port.

In some embodiments, the transmission interface may further include a second adapter board. At least a portion of the second adapter board may be located in the mother base, a side of the second adapter board may protrude through the mounting port to an outer side of the mother base, and the second adapter board may be provided with a plurality of third holes for fixing the plurality of contact points.

In some embodiments, the mother base may further include a second circuit board. The second circuit board may be connected to a side of the second adapter board back from the end portions of the plurality of contact points in contact with the plurality of pop pins to cause the plurality of contact points to be connected with a wire of the second circuit board, and the second circuit board may be fixedly connected with a housing of the mother base.

In some embodiments, the signal acquisition device may further include a conducting wire. One end of the conducting wire may be electrically connected with the sensor, and another end of the conducting wire may be connected with the plurality of contact points via the wire of the second circuit board.

In some embodiments, the second circuit board may be provided with a plurality of fourth holes located on a peripheral side of the second adapter board, the wire of the second circuit board may extend from the plurality of fourth holes toward the plurality of contact points, the conducting wire may be fixed at the plurality of fourth holes and electrically connected with the wire of the second circuit board at the plurality of fourth holes.

In some embodiments, the sub-base may include a first magnet, and the first magnet may be located in the sub-base. The mother base may include a second magnet, and the second magnet may be located in the mother base. The first magnet and the second magnet attract each other to cause the sub-base to be connected with the mother base.

In some embodiments, the sub-base may be detachably connected with the mother base by a snap.

In some embodiments, a side wall of the raised structure and a side wall of the groove corresponding to the side wall of the raised structure may be provided with a matching slide groove and a matching guide rail, respectively.

In some embodiments, the signal acquisition device may be distributed in the wearable object at locations corresponding to the chest, the shoulders, the abdomen, the waist, or the thighs of the user.

In some embodiments, the physiological signal may include at least one of an electromyographic signal, a postural signal, an electrocardiographic signal, a respiratory signal, a temperature signal, and a humidity signal.

DETAILED DESCRIPTION

Figure 1:
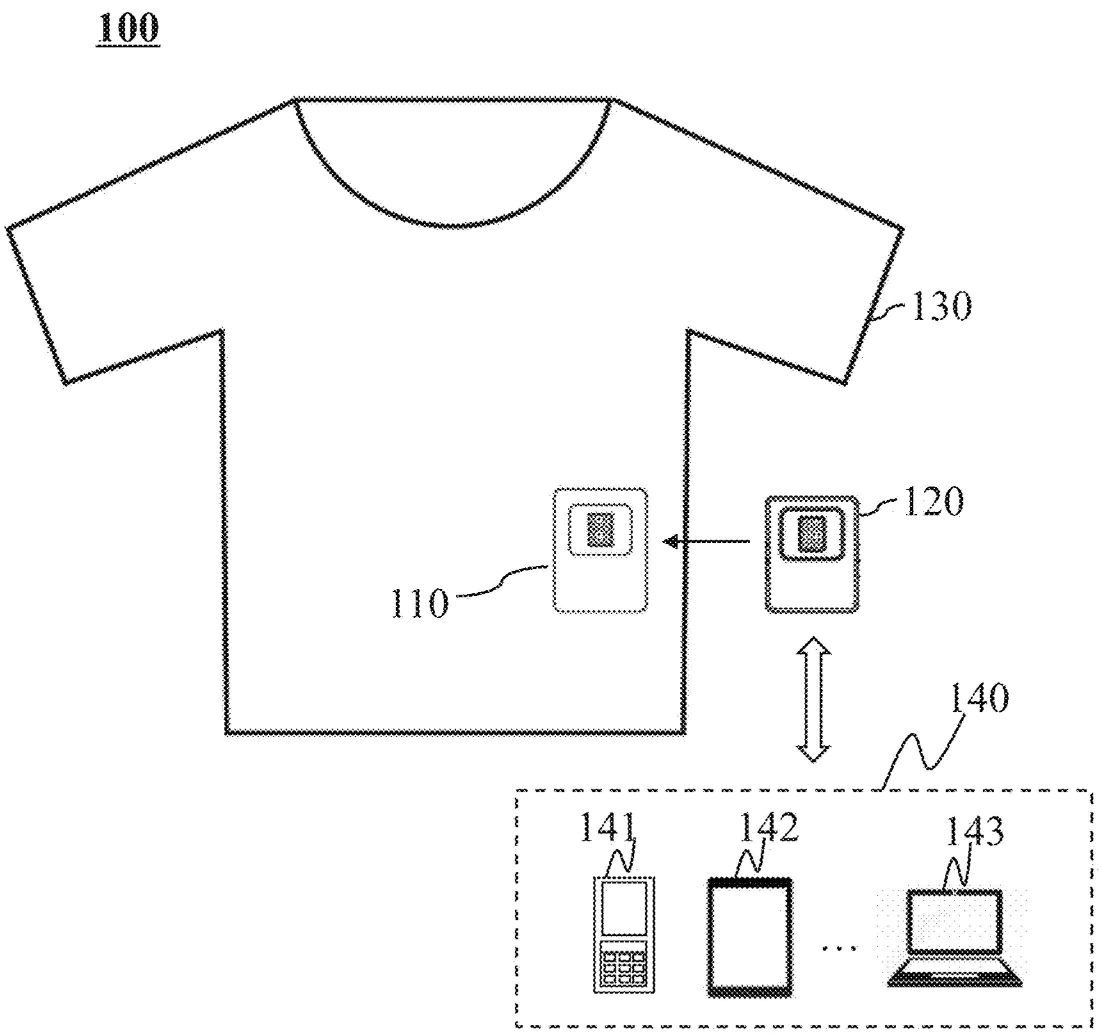
FIG. 1 is a diagram illustrating an exemplary application scenario of a signal acquisition device according to some embodiments of the present disclosure.

To more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that “system”, “device”, “unit” and/or “module” as used herein is a manner used to distinguish different components, elements, parts, sections, or assemblies at different levels. However, if other words serve the same purpose, the words may be replaced by other expressions.

As shown in the present disclosure and claims, the words “one”, “a”, “an” and/or “the” are not especially singular but may include the plural unless the context expressly suggests otherwise. In general, the terms “comprise”, “comprises”, “comprising”, “include”, “includes”, and/or “including”, merely prompt to include operations and elements that have been clearly identified, and these operations and elements do not constitute an exclusive listing. The methods or devices may also include other operations or elements.

The use of the words “first,” “second,” or the like in the present disclosure and the claims does not indicate any order or importance, but is merely used to distinguish different components. Similarly, the words “one” or “a”, etc., do not indicate a quantitative limitation, but rather indicate the presence of at least one component. Unless otherwise stated, “anterior”, “posterior”, “lower,” and/or “upper” and similar terms are for illustrative purposes only and are not limited to a location or a spatial orientation.

Embodiments of the present disclosure provide a signal acquisition device. In some embodiments, the signal acquisition device may include a wearable object provided with a sensor, a sub-base, and a mother base. The wearable object may be configured to be worn by a user to acquire a physiological signal from the user via the sensor. In some embodiments, the mother base is fixed on the wearable object, and the sub-base is detachably connected with the mother base. The mother base includes a transmission interface. In some embodiments, signal output ends of a plurality of sensors (e.g., a myoelectric sensor, a temperature sensor, an inertial sensor, a stress sensor, etc.) may be integrated in the transmission interface. In some embodiments, the sub-base may be configured to accommodate a circuit structure. The circuit structure includes a power supply circuit and a signal transmitter. When the mother base is connected with the sub-base, the circuit structure is electrically connected with the sensors via the transmission interface. The power supply circuit may supply power to at least a portion of the sensors, and the sensors may also transmit the physiological signal to the circuit structure of the sub-base. The signal transmitter may send the physiological signal to an external device (e.g., a mobile device, a tablet computer, a laptop, a desktop computer, etc.). When the user wears the wearable object for exercise, the user connects the sub-base, which is originally separate from the mother base, with the mother base, and the circuit structure of the sub-base is electrically connected with the the sensor via the transmission interface of the mother base, thus the sensor on the wearable object may collect the physiological signal of the user in real time. The wearable object often needs to be washed. The sub-base may be removed from the mother base, and only the whole wearable object (including the mother base and the sensor) may be cleaned. By setting the mother base and the sub-base, which provides power to at least a portion of the sensors and acquires and processes signals, in a detachable connection, separate cleaning of the wearable object and the mother base may be realized, avoiding damage to sub-base with a complex circuit structure and a high cost while meeting the cleaning needs of the wearable object.

FIG. 1 is a diagram illustrating an exemplary application scenario of a signal acquisition device according to some embodiments of the present disclosure. As shown in FIG. 1, an application scenario 100 of a signal acquisition device may include a wearable object 130, a mother base 110, a sub-base 120, and an external device 140.

The wearable object 130 is configured to be worn by a user. In some embodiments, the wearable object 130 may be a top (e.g., a t-shirt, an undershirt, a tank top, a jacket, etc.) that is worn on the upper body of the user. In some embodiments, the wearable object 130 may be pants (e.g., trousers, shorts, etc.) worn on the lower body of the user. In some embodiments, the wearable object 130 may also be a leg ring or a belt worn on the leg or the waist of the user, respectively. In some embodiments, the wearable object 130 may be provided with one or more sensors, and different types of sensors may be configured to acquire different physiological signals from the user. In some embodiments, the sensor may include one or more of a myoelectric sensor, a stress sensor, an electrocardiogramansor, a blood oxygen sensor, a blood pressure sensor, an inertial sensor, a respiratory sensor, a temperature sensor, a humidity sensor, etc. In some embodiments, the physiological signal may include one or more of an electromyographic signal, a postural signal, an electrocardiogramaignal, a blood oxygen signal, a blood pressure signal, a respiratory signal, a temperature signal, a humidity signal, or the like. The sensor may fit against the skin of the user or not. For example, electrodes of the myoelectric sensor need to fit against the skin of the user, and an end of the myoelectric sensor back away from the electrodes may be connected with the wearable object. As another example, the inertial sensor may not fit against the skin of the user, and the inertial sensor may be located on an outer surface, an inner surface, or between layers of fabric of the wearable object.

The mother base 110 is configured to implement an electrical connection between the sensor and the sub-base 120. In some embodiments, the mother base 110 may be fixed on the wearable object 130, a transmission interface is provided on the mother base 110, and a signal output end of the sensor is integrated on the transmission interface. For example, different sensors may be electrically connected with the mother base 110 via different wires, one end of each of the different wires may be connected with each of the different sensors, and another end of each of the different wires may be located at the mother base 110 and integrated on the transmission interface. The sensor may be electrically connected with a circuit structure of the sub-base 120 via the transmission interface. In some embodiments, the mother base 110 may be fixed on the wearable object 130 by bonding, snap-fitting, inlay, etc. For example, the mother base 110 may be fixed on the wearable object 130 by a snap connection. In some embodiments, a plurality of elastic tabs are fixed on a side surface of the mother base 110 proximate to the wearable object 130. One end of each of the elastic tabs is fixed on the mother base 110, and another end of each of the elastic tabs passes through the wearable object 130 and is bent toward the mother base 110. At this time, the clastic tab forms a two-segment structure that is nearly vertical. A first segment of the clastic tab is connected with the mother base 110 and passes through the wearable object 130, and a second segment of the clastic tab crimps a portion of the wearable object 130 to the mother base, realizing the fixation of the mother base 110 with the wearable object 130. In some embodiments, the mother base 110 is provided with a plurality of threaded holes on the side surface proximate to the wearable object 130. Tip spikes of screws are threadedly connected with the threaded holes on the mother base 110 after passing through the wearable object 130, realizing the fixation of the mother base 110 with the wearable object 130. In some embodiments, the mother base 110 may be fixed on a region on the wearable object 130 corresponding to a portion of the user, such as the chest, the shoulders, the abdomen, the waist, or the thigh. More descriptions regarding the mother base 110 may be found in FIG. 3, FIG. 6A, FIG. 6B, FIG. 7, and elsewhere in the present disclosure.

The sub-base 120 is disposed independently with respect to the mother base 110 and is configured to accommodate the circuit structure. In some embodiments, the circuit structure may include a power supply circuit and a signal transmitter. When the mother base 110 is connected with the sub-base 120, the circuit structure is electrically connected with the sensor via the transmission interface of the mother base 110. The power supply circuit may supply power to at least a portion of the sensor, the sensor may acquire the physiological signal of the user and transmit the acquired physiological signal to the sub-base via the transmission interface, and the signal transmitter may send the processed physiological signal to the external device 140. In some embodiments, the circuit structure may include a transmission plug adapted to the transmission interface. The transmission plug may be provided on the sub-base 120, and the transmission plug may be electrically connected with the circuit structure (e.g., the power supply circuit and the signal transmitter) within the sub-base 120. When the mother base 110 is connected with the sub-base 120, the transmission plug is electrically connected with the transmission interface. In some embodiments, the circuit structure of the sub-base 120 may include a signal processing unit, and the signal processing unit may process the received physiological signal to form physiological data. In some embodiments, the signal processing unit may include an amplification circuit, and the amplification circuit may amplify the physiological signal. In some embodiments, the signal processing unit may include a denoising circuit, and the denoising circuit may perform a denoising process on the physiological signal. In some embodiments, the signal processing unit may include a conversion circuit, and the conversion circuit may convert an analog signal into a digital signal that may be received by the external device. In some embodiments, the circuit structure may also include a memory, and the memory is configured to store the received physiological signal. The physiological signal collected by the sensor may promptly enter into the circuit structure of the sub-base for storage and processing, which ensures the integrity and authenticity of the physiological signal.

In some embodiments, the sub-base 120 may be detachably connected with the mother base 110, facilitating the cleaning of the mother base 110 and the wearable object 130. In some embodiments, a groove is provided on a side of the mother base 110 back away from the wearable object 130, and at least a portion of the sub-base 120 may be snapped to the mother base 110 through the groove (as shown in FIGS. 2-9), ensuring that the sub-base 120 is detachably connected with the mother base 110. For example, the sub-base 120 is integrally embedded in the groove of the mother base 110 to be snapped to the mother base 110, ensuring that the sub-base 120 is detachably connected with the mother base 110. As another example, the sub-base 120 is provided with a raised structure, and the raised structure of the sub-base is embedded in the groove of the mother base 110 to be snapped to the mother base 110, ensuring that the sub-base 120 is detachably connected with the mother base 110. In some embodiments, the sub-base 120 may be detachably connected with the mother base 110 through a slide groove and a guide rail. More descriptions regarding the slide groove and the guide rail may be found in FIG. 5-FIG. 9 and related descriptions thereof. In some embodiments, the sub-base 120 may be detachably connected with the mother base 110 by a snap. In some embodiments, the sub-base 120 may be magnetically connected with the mother base 110, ensuring that the sub-base 120 is detachably connected with the mother base 110. Specifically, a first magnet is located in the sub-base 120 and a second magnet is located in the mother base 110. The first magnet and the second magnet may attract each other to cause the sub-base 120 to be magnetically connected with the mother base 110. More descriptions regarding the first magnet and the second magnet may be found in FIG. 7 and FIG. 9 and related descriptions thereof. In some embodiments, the sub-base 120 may be detachably connected with the mother base 110 by the snap connection and magnetic attraction, which is conducive to maintaining a stable connection between the mother base 110 and the sub-base 120 and preventing the mother base 110 and the sub-base 120 from moving relative to each other due to strenuous movements of the user when wearing the signal acquisition device. The sub-base 120 may also be detachably connected with the mother base 110 in a plurality of other possible ways, which are not limited herein.

In some embodiments, the sub-base 120 may be connected with the external device via a network (e.g., a wired network or a wireless network) or a communication cable to enable transmission and exchange of information and/or data. For example, the sub-base 120 may transmit the physiological data (i.e., the processed physiological signal) to the external device 140 via the wireless network. More descriptions regarding the sub-base 120 may be found in descriptions in FIG. 4, FIG. 8A, FIG. 8B, FIG. 9, and elsewhere in the present disclosure.

The external device 140 is configured to process the physiological data. In some embodiments, the external device 140 may store, count, analyze the physiological data, or process the physiological data in other ways. In some embodiments, the external device 140 may have one or more functions such as data processing, display, voice playback, communication, or the like. In some embodiments, the external device 140 may include a mobile device 141, a tablet 142, a laptop 143, a desktop computer, or the like. In some embodiments, the user may enter specific processing instructions (e.g., an instruction of calculating an average value of the blood pressure collected for a plurality of times over a certain time period) to the external device 140.

It should be noted that the application scenario of the signal acquisition device is provided for illustrative purposes only and is not intended to limit the scope of the present disclosure. For a person of ordinary skill in the art, a variety of modifications or variations may be made according to the description of the present disclosure. However, these modifications or variations do not depart from the scope of the present disclosure.

Figure 2:
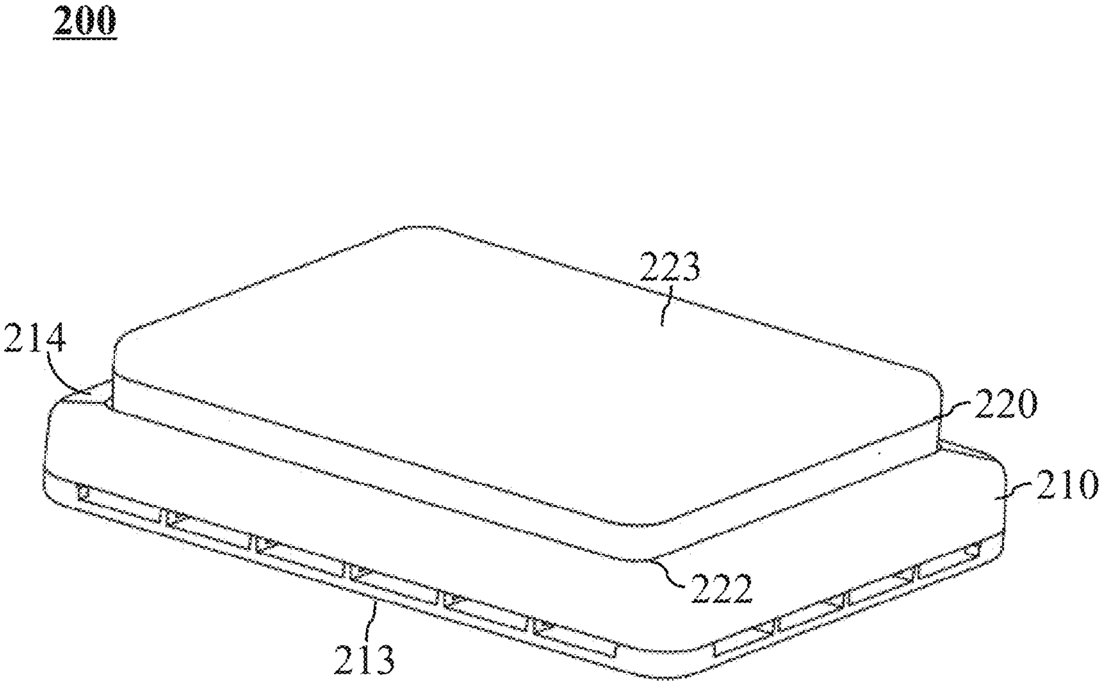
FIG. 2 is a schematic diagram illustrating a structure of a signal acquisition device according to some embodiments of the present disclosure.
Figure 3:
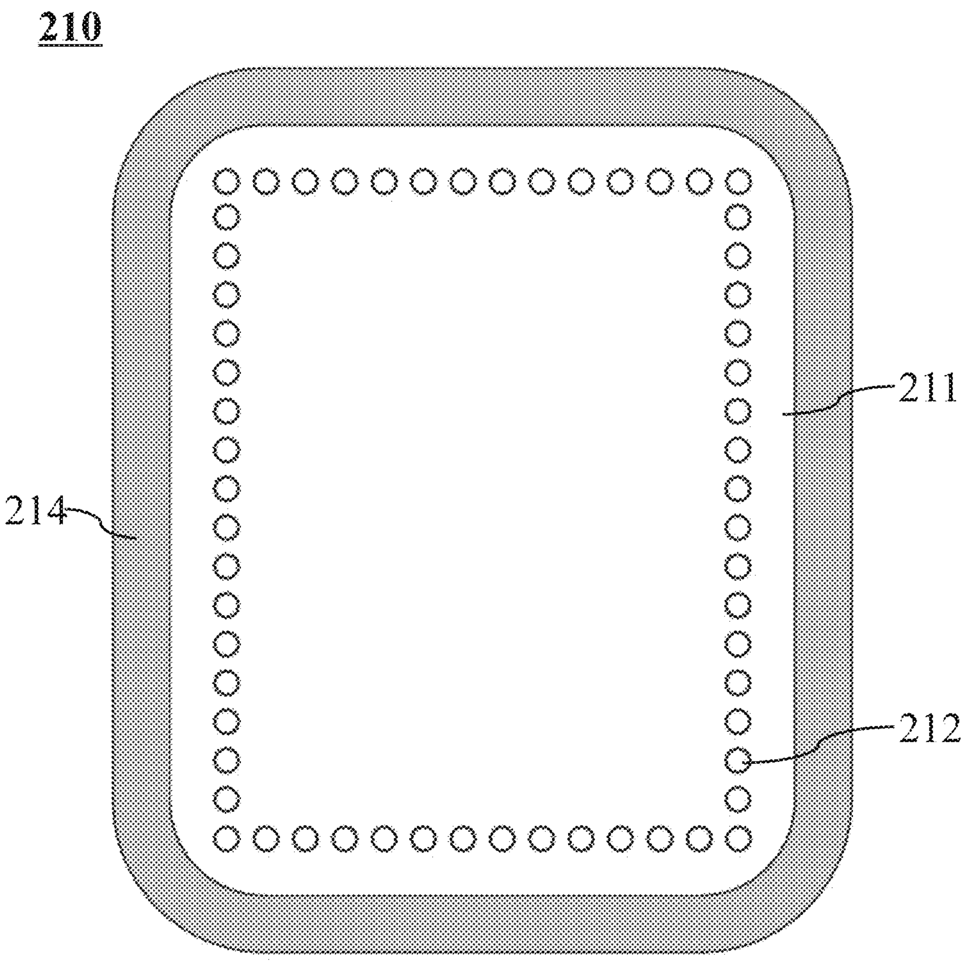
FIG. 3 is a schematic diagram illustrating a structure of a mother base according to some embodiments of the present disclosure.
Figure 4:
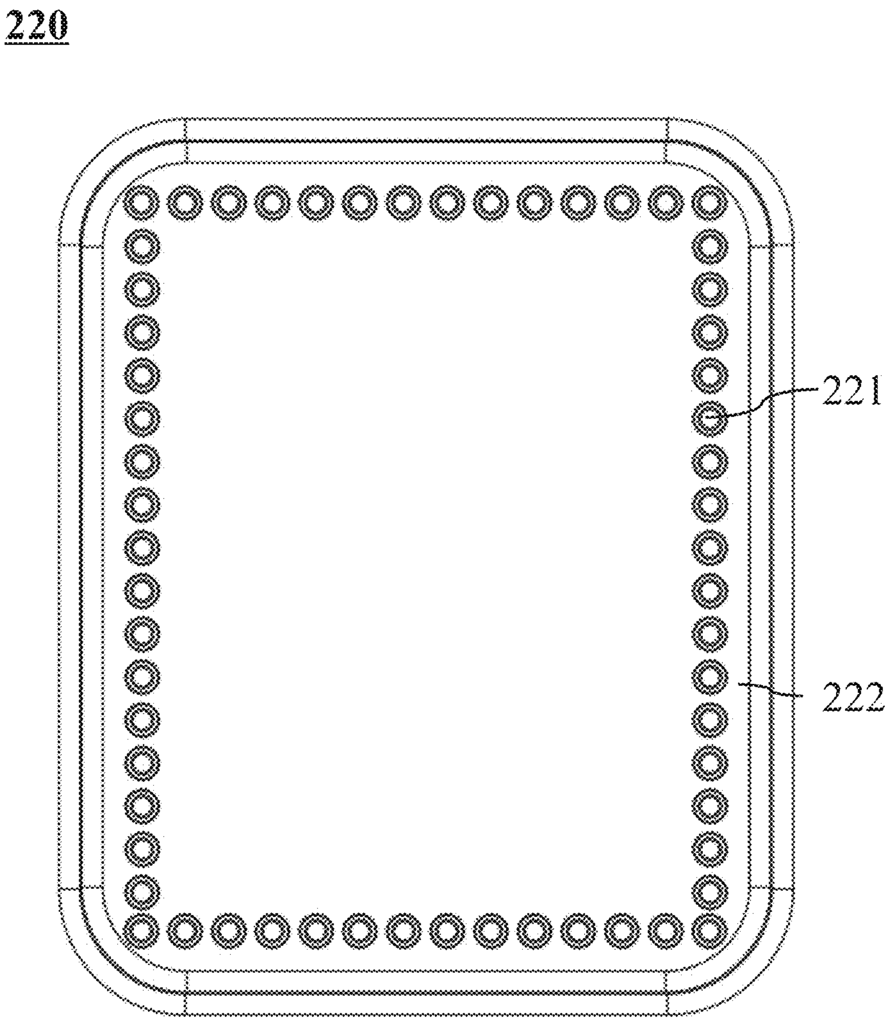
FIG. 4 is a schematic diagram illustrating a structure of a sub-base according to some embodiments of the present disclosure.

The signal acquisition device may be exemplarily described below in conjunction with FIG. 2-FIG. 4. FIG. 2 is a schematic diagram illustrating a structure of a signal acquisition device according to some embodiments of the present disclosure. FIG. 3 is a schematic diagram illustrating a structure of a mother base according to some embodiments of the present disclosure. FIG. 4 is a schematic diagram illustrating a structure of a sub-base according to some embodiments of the present disclosure. As shown in conjunction with FIGS. 2-4, in some embodiments, a signal acquisition device 200 may include a mother base 210 and a sub-base 220. The mother base 210 may be of a rectangular structure, which may include a first side portion 213 and a second side portion 214 oppositely disposed. The first side portion 213 is connected with a wearable object (not shown in FIGS. 2-4), and the second side portion 214 is connected with the sub-base 220. In some embodiments, a groove 211 is provided at the second side portion 214 of the mother base 210. A shape of the sub-base 220 is approximately the same as a shape of the groove 211, and a size (e.g., a length or a width) of the groove 211 is slightly larger than a size of the sub-base 220 to cause the whole sub-base 220 to be embedded in the groove 211. In some embodiments, the sub-base 220 may include a third side portion 222 and a fourth side portion 223 oppositely disposed, and the third side portion 222 is connected with the mother base 210. In some embodiments, the transmission interface may be provided within the groove 211, and the transmission plug is provided at the third side portion 222 of the sub-base 220. The sub-base 220 is embedded in the groove 211 to cooperate with the mother base 210, and the transmission interface is electrically connected with the transmission plug. Thus, a physiological signal of a user acquired by a sensor may be transmitted through the connection between the transmission interface and the transmission plug to a circuit structure of the sub-base 220.

In some embodiments, the mother base 210 may be of a rectangular structure. In other embodiments, the mother base 210 may also be of a cylindrical structure or other shaped structure. In some embodiments, the groove 211 on the mother base 210 may be a rectangular groove 211, and the sub-base 220 is a rectangular structure adapted to the rectangular groove 211. In some embodiments, the groove 211 disposed on the mother base 210 may also be a circular groove 211, and the sub-base 220 is a cylindrical structure adapted to the circular groove 211. In other embodiments, the groove 211 disposed on the mother base 210 may also be a groove 211 of other possible shapes (e.g., triangular, star, hexagonal, etc.), for example, the shape of the sub-base 220 fits the shape of the groove 211. In some embodiments, to facilitate assembling and detaching the sub-base 220 relative to the mother base 210, after the sub-base 220 is embedded in the groove 211, a portion of the sub-base 220 may protrude relative to the second side portion of the mother base 210, and a protruding portion of the sub-base 220 relative to the mother base 210 may be used to hold the sub-base 220 when assembling and detaching the sub-base 220.

In some embodiments, the transmission plug may include a plurality of pop pins 221, and the transmission interface may include a plurality of contact points 212, and the plurality of contact points 212 are correspondingly aligned with the plurality of pop pins 221 in a one-to-one manner. In some embodiments, for each of the plurality of pop pins 221, one end of the pop pin 221 is electrically connected with the circuit structure of the sub-base 220, and another end of the pop pin 221 is exposed, to contact the contact points 212. In some embodiments, the pop pin 221 may be an electrically conductive material (e.g., an electrically conductive metallic material) to receive and transmit the physiological signal. In some embodiments, the contact point 212 may be a portion of an electrically conductive metallic structure. For example, the contact point 212 may be an end portion, a side surface, a lateral, or any point of the metallic structure. An end of the metallic structure away from the contact point 212 is electrically connected with a signal output end of the sensor. In some embodiments, the metallic structure may be a metal post structure or a metal sheet structure. In some embodiments, a material of the pop pin 221 may include but is not limited to, one or more of gold, silver, copper, iron, tin, aluminum, or the like, and a material of the contact point 212 may be the same as or different from the material of the pop pin 221. When the transmission plug is electrically connected with the transmission interface, end portions of the plurality of contact points 212 are in contact with end portions of the plurality of pop pins 221 one by one. One contact point 212 is electrically connected with one signal output end of a sensor, and a physiological signal acquired by the sensor is transmitted to the circuit structure of the sub-base 220 through the electrical connection of one pop pin 221 and one contact point 212. In other words, a plurality of physiological signals acquired by a plurality of sensors are transmitted in one-to-one correspondence with pathways formed by connection of the plurality of pop pins 221 and the plurality of contact points 212. In some embodiments, the pop pins 221 may have elasticity along a direction of the pop pins 221 connecting with the contact points 212 such that, even if there is a slight wobble between the transmission interface and the transmission plug, the pop pins 221 may remain in contact with the contact points 212. In some embodiments, the pop pins 221 may include a needle, a spring, and a syringe provided coaxially. The spring is provided inside the syringe, with one end of the needle provided inside the syringe and connected with the spring, and the other end of the needle exposed to the syringe to be in contact with the contact points 212. The contact points 212 are in contact with the pop pins 221 and squeeze the pop pins 221. At this time, the needle squeezes the spring, so that the spring is in a compressed state. When there is a slight wobble between the transmission interface and the transmission plug, a compression degree of the spring may be adjusted accordingly, so that the pop pins 221 always remain in contact with the contact points 212 under the clastic force of the spring. In some embodiments, as shown in FIG. 3, the plurality of contact points 212 may be located on a side wall at a bottom of the groove 211. As shown in FIG. 4, the plurality of pop pins 221 may be located on the third side portion 222 of the sub-base 220. When the whole sub-base 220 is embedded in the groove 211, the contact points 212 at the bottom of the groove 211 are contacted with the pop pins 221 on the third side portion 222 of the sub-base 220 one by one. In some embodiments, the plurality of contact points 212 may also be located on a side wall of a side portion of the groove 211, and the plurality of pop pins 221 may be located on a side wall of the sub-base 220 adjacent to the third side portion 222 or the fourth side portion 223. When the whole sub-base 220 is embedded in the groove 211, the contact points 212 located on the side wall of the groove 211 are contacted with the pop pins 221 located on the side wall of the sub-base 220 one by one. In some embodiments, the plurality of contact points 212 may be provided at intervals along an edge of the groove 211. In some embodiments, the plurality of contact points 212 may also be distributed in an array (e.g., a rectangular array, a circular array, a triangular array, etc.) on a bottom wall of the groove 211. In some embodiments, the plurality of contact points 212 may also be distributed in a straight line or a curved line. The plurality of contact points 212 may also be distributed in other possible forms. It is to be known that positions of the pop pins 221 and the contact points 212 may be set interchangeably. In other words, the pop pins 221 may be set inside the groove 211, and the signal output end of the sensor may be electrically connected with the pop pins 221, and the contact points 212 may be provided on the third side portion 222 of the sub-base 220.

Figure 5:
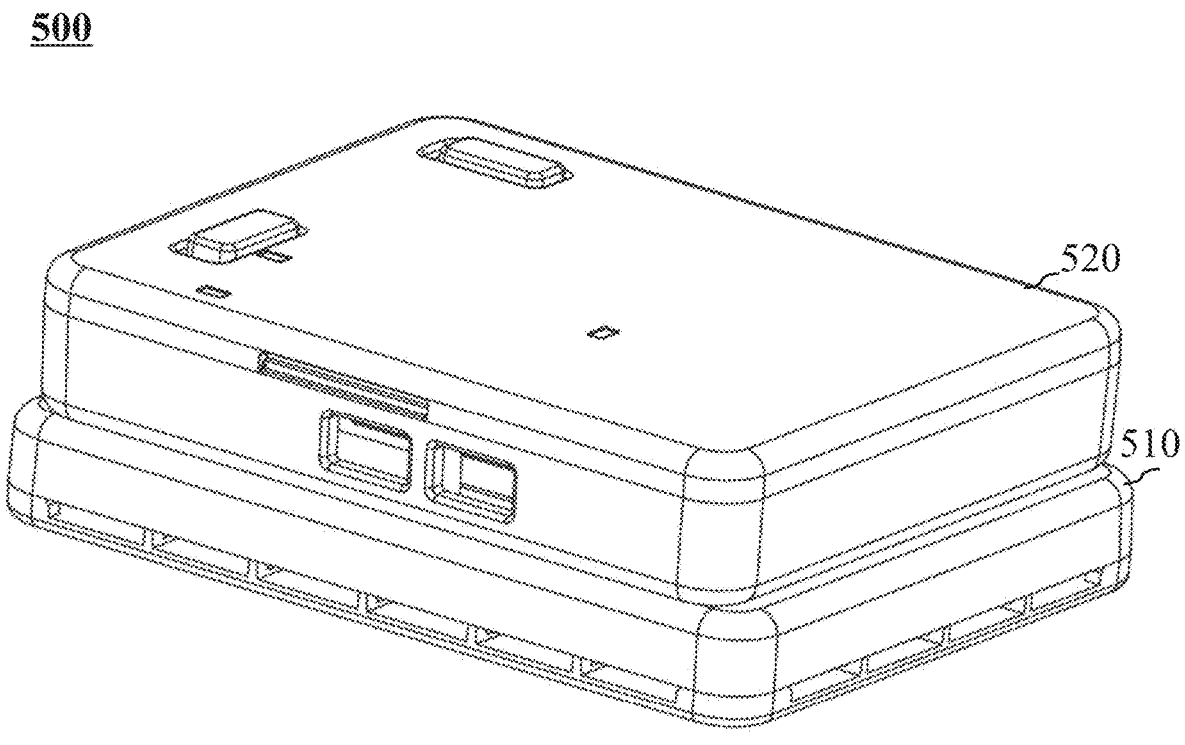
FIG. 5 is a schematic diagram illustrating a structure of a signal acquisition device according to some embodiments of the present disclosure.
Figure 6A:
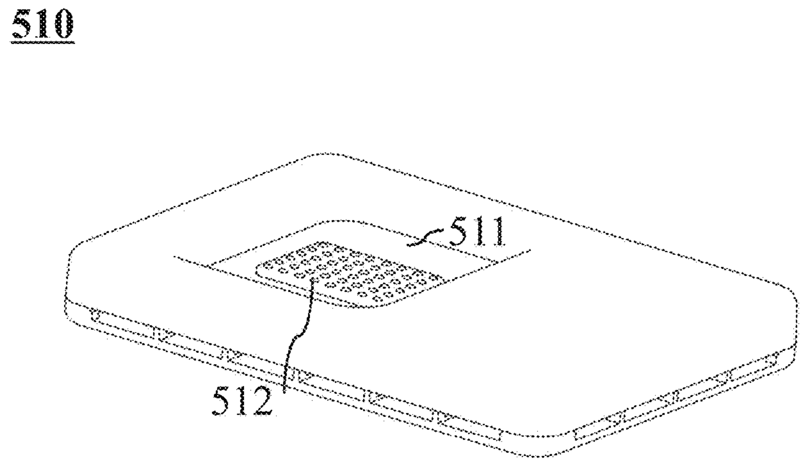
FIG. 6A is a schematic diagram illustrating a structure of a mother base according to some embodiments of the present disclosure.
Figure 6B:
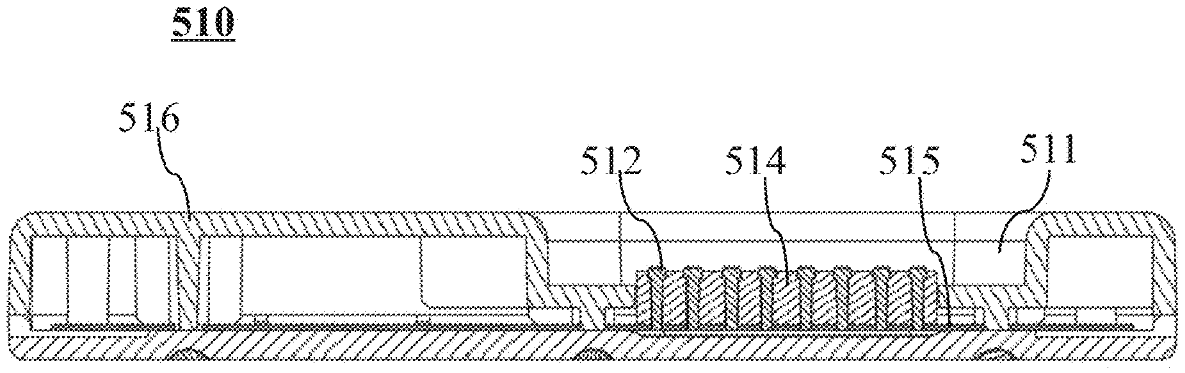
FIG. 6B is a diagram illustrating a cross-section of a mother base according to some embodiments of the present disclosure.
Figure 7:
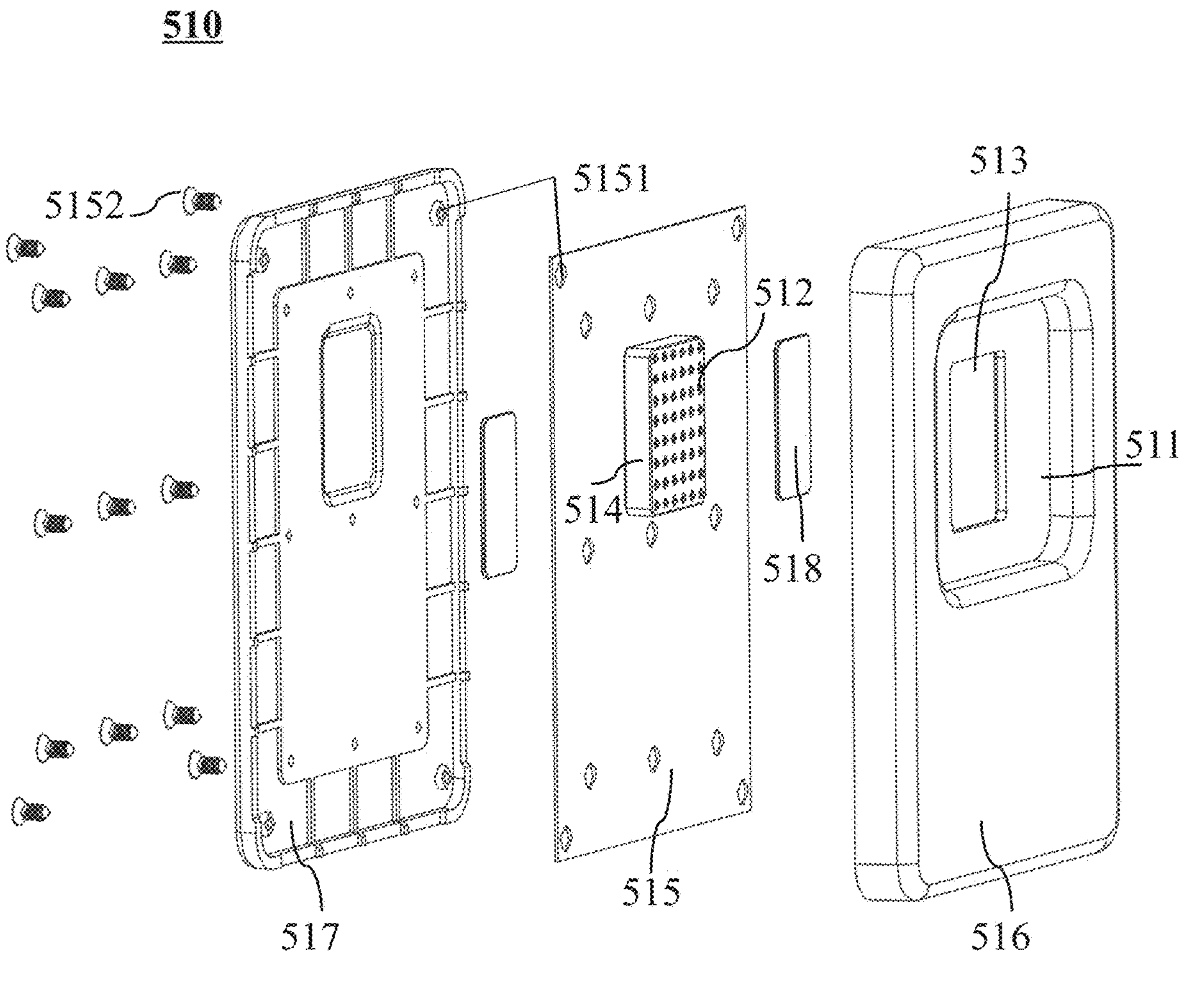
FIG. 7 is an exploded diagram illustrating a mother base according to some embodiments of the present disclosure.
Figure 8A:
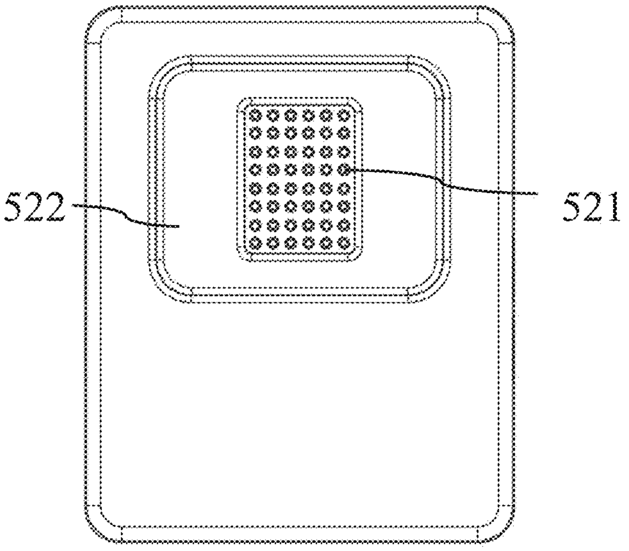
FIG. 8A is a schematic diagram illustrating a structure of a sub-base according to some embodiments of the present disclosure.
Figure 8B:
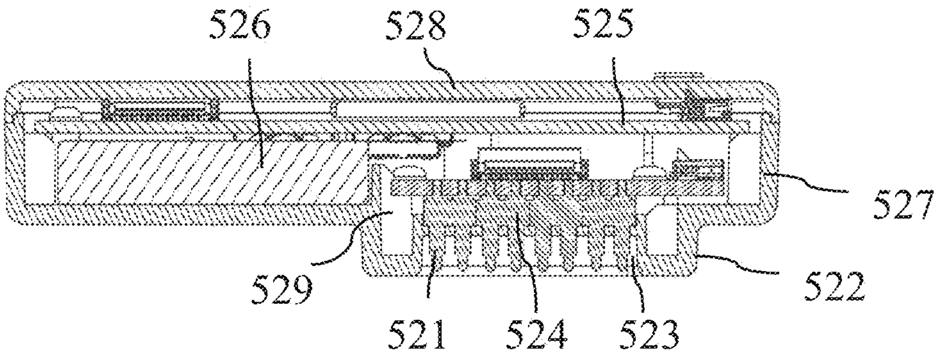
FIG. 8B is a diagram illustrating a cross-section of a sub-base according to some embodiments of the present disclosure.
Figure 9:
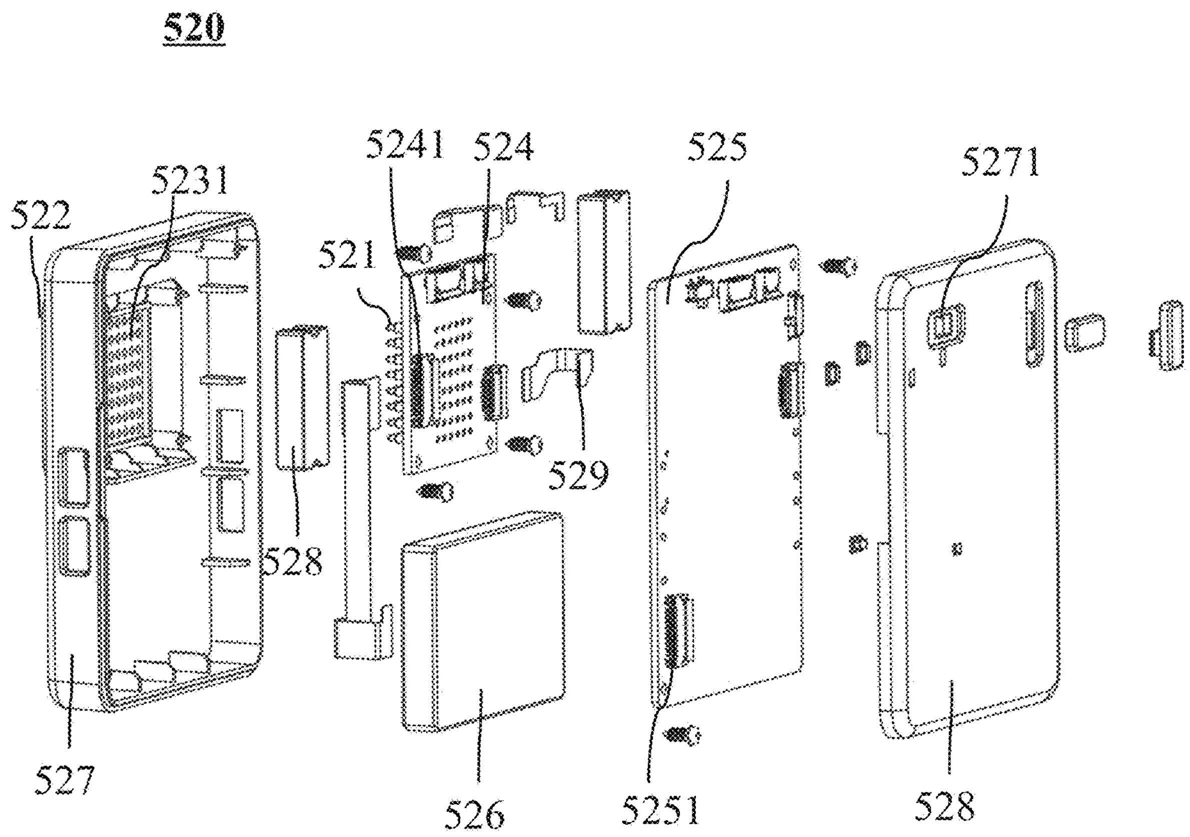
FIG. 9 is an exploded diagram illustrating a sub-base according to some embodiments of the present disclosure.

A further exemplary illustration of the signal acquisition device may be provided below in conjunction with FIG. 5-FIG. 9. FIG. 5 is a schematic diagram illustrating a structure of a signal acquisition device according to some embodiments of the present disclosure. FIG. 6A is a schematic diagram illustrating a structure of a mother base according to some embodiments of the present disclosure. FIG. 6B is a diagram illustrating a cross-section of a mother base according to some embodiments of the present disclosure. FIG. 7 is an exploded diagram illustrating a mother base according to some embodiments of the present disclosure. FIG. 8A is a schematic diagram illustrating a structure of a sub-base according to some embodiments of the present disclosure. FIG. 8B is a diagram illustrating a cross-section of a sub-base according to some embodiments of the present disclosure. FIG. 9 is an exploded diagram illustrating a sub-base according to some embodiments of the present disclosure.

In conjunction with what is shown in FIG. 5-FIG. 9, a signal transmission device 500 may include a mother base 510 and a sub-base 520. The mother base 510 is provided with a groove 511, the sub-base 520 is provided with a raised structure 522 adapted to the groove 511, and the raised structure 522 projects outwardly relative to a body of the sub-base 520. A transmission interface is provided at the groove 511, the transmission plug is provided on the raised structure 522, and the raised structure 522 is embedded in the groove 511 to be mated with the groove 511. The transmission interface is electrically connected with a transmission plug so that a physiological signal of a user acquired by a sensor may be transmitted to a circuit structure of the sub-base 520 through the connection between the transmission interface and the transmission plug. In some embodiments, the transmission interface includes a plurality of integrated contact points 512, and the transmission plug includes a plurality of integrated pop pins 521. The plurality of integrated contact points 512 and the plurality of integrated pop pins 521 form an integral module, respectively. The plurality of integrated pop pins 521 on the integral module and the plurality of integrated contact points 512 on the integral module are distributed in a one-to-one corresponding array, which facilitates one-to-one alignment and contact of the contact points 512 and the pop pins 521, and also facilitates alignment of the contact points 512 and the pop pins 521. When the transmission plug is electrically connected with the transmission interface, the integral module formed by the plurality of contact points 512 is aligned with the integral module formed by the plurality of pop pins 521, with the contact points 512 and the pop pins 521 thereon in one-to-one contact. In some embodiments, the integral module formed by the plurality of contact points 512 and the integral module formed by the plurality of pop pins 521 are approximately of the same shape and size, and arrays of the plurality of contact points 512 and the plurality of pop pins 521 are distributed in the same way, to facilitate alignment of the integral module formed by the contact points 512 with the integral module formed by the plurality of pop pins 521. More descriptions regarding the pop pins 521 and the contact points 512 may be found in FIG. 2-FIG. 4 and related descriptions thereof.

In conjunction with FIG. 6B and FIG. 7, the mother base 510 may include a first mother base housing 516 and a second mother base housing 517, the first mother base housing 516 and the second mother base housing 517 are spliced together to form a body of the mother base having a mounting cavity provided inside. In some embodiments, to prevent cleaning liquids from entering the mother base 510 during the cleaning of the wearable object or sweat stains on the user's body from entering the mother base 510 when the user wears the wearable object, the first mother base housing 516 and the second mother base housing 517 may be directly sealed to improve the waterproof performance of the mother base 510. For example, a seal may be provided between the first mother base housing 516 and the second mother base housing 517. In some embodiments, the groove 511 is provided at the first mother base housing 516, a mounting port 513 is provided on a side wall at a bottom of the groove 511, and the transmission interface is embedded in the groove 511 through the mounting port 513. In some embodiments, the transmission interface may include a plurality of contact points 512 distributed in an array.

In some embodiments, the transmission interface may further include a second adapter board 514. The second adapter board 514 is fixed within the mounting port 513 and provided with a plurality of third holes (not shown in the figures) for fixing the plurality of contact points 512. The plurality of third holes are distributed in an array and provided in one-to-one correspondence with the plurality of contact points 512. In some embodiments, the contact points 512 may be metal posts fixed within the third holes, and one end of each of the metal posts is exposed to the second adapter board 514 and may be in contact with each of the pop pins 521. In some embodiments, at least a portion of the second adapter board 514 is provided within the mother base 510, and a side of the second adapter board 514 having the contact points 512 extends through the mounting port 513 to the exterior of the mother base 510. In some embodiments, a gap between a peripheral side of the second adapter board 514 and the side wall of the groove 511 corresponding to the mounting port 513 may be filled with a waterproof material (e.g., epoxy, plastic, silicone, etc.) or provided with a sealing ring to further improve the waterproof performance of the mother base 510.

In some embodiments, the mother base 510 may also include a first circuit board 515, the first circuit board 515 is provided in the mounting cavity of the mother base 510, and the first circuit board 515 is connected with a side of the second adapter board 514 back from an end portion of the plurality of contact points 512 in contact with the plurality of pop pins 521. In some embodiments, the first circuit board 515 is fixedly connected with the mother base 510. Specifically, the first circuit board 515 is fixedly connected with the second mother base housing 517 by threads. A plurality of threaded holes 5151 are correspondingly provided on the first circuit board 515 and the second mother base housing 517, and screws 5152 are sequentially passed through the threaded holes 5151 on the second mother base housing 517 and the first circuit board 515 to realize the fixing of the first circuit board 515 and the second mother base housing 517.

In some embodiments, the signal acquisition device may include one or more conducting wires (not shown in the figures), one end of each conducting wire is electrically connected with one sensor, and another end of each conducting wire is connected with one contact point 512 through a wire of the first circuit board 515. The conducting wires are laid or buried in the wearable object, and the physiological signal acquired by the sensor is sequentially transmitted to the sub-base 520 through the conducting wires, the wire of the first circuit board 515, the contact points 512, and the pop pins 521. The plurality of contact points 512 are arranged in an array. A distance between two adjacent contact points 512 is small, each conducting wire needs to be electrically connected with one contact point, and a distance between connection regions of different conducting wires and corresponding contact points is too small, resulting in higher difficulty in the production of the signal acquisition device. Each connection region may come into contact, affecting the accurate transmission of the physiological signal and even leading to short-circuit problems in the circuit. In such a case, in some embodiments, a plurality of fourth holes (not shown in the figures) are provided on a position of the first circuit board 515 corresponding to a peripheral side of the second adapter board 514, the wire of the first circuit board 515 extends from the fourth holes toward the contact points 512, and the wire of the first circuit board 515 is electrically connected with the contact points 512 (the metal post), respectively. The conducting wires are fixed at the fourth holes and electrically connected with the wire of the first circuit board 515 at the fourth holes. The physiological signal transmitted via the conducting wires is passed to the contact points 512 via the wire at the fourth holes in the first circuit board 515, which may realize the physiological signal acquired by the sensor to be gathered in the mother base 510 on the wearable object and to be uniformly transmitted through the mother base 510 to the sub-base 520. Furthermore, such a setting may reduce the difficulty of production of the signal acquisition device, and may also prevent problems such as confusion in physiological signal transmission and short circuit caused by contact between each conducting wire with each contact poin. In some embodiments, the conducting wires may also be directly electrically connected with the contact points 512 without being electrically connected with the contact points 512 through the circuit of the first circuit board 515.

In order to further improve the waterproof performance of the mother base 510, and to prevent the signal acquisition device from damaging the first circuit board 515 when the signal acquisition device is cleaned or when sweat stains soak into the interior of the mother base 510, in some embodiments, before the encapsulation of the mother base 510, an epoxy resin is filled inside the mother base 510 to wrap the first circuit board 515 to play a role of waterproof and sweatproof. In some embodiments, a surface of the first circuit board 515 may be coated with materials such as triple-proof paint, nano-coating, or the like, to improve the waterproof and sweatproof performance of the first circuit board 515.

In conjunction with FIG. 8B and FIG. 9, the sub-base 520 may include a first sub-base housing 527 and a second sub-base housing 528, the first sub-base housing 527 and the second sub-base housing 528 are collocated to form the sub-base having a mounting cavity provided inside, and the mounting cavity is provided with the circuit structure. In some embodiments, the raised structure 522 is provided at the first sub-base housing 527, and the raised structure 522 may include a recessed portion 523, and the recessed portion 523 is located on a side of the raised structure 522 away from the first sub-base housing 527. In some embodiments, a bottom wall of the recessed portion 523 may be provided with a plurality of first holes 5231, the plurality of first holes 5231 corresponding one-to-one with the plurality of pop pins 521. In some embodiments, at least a portion of the pop pins 521 may protrude through the plurality of first holes 5321 to an outer side of the sub-base 520. Each of the first holes 5231 has a size that is slightly larger than a diameter of each of the pop pins 521, and when the pop pins 521 extend from the first holes 5231, the first holes 5231 may serve to fix the integral module formed by the pop pins 521. When the raised structure 522 is embedded in the groove 511 to fit together, the pop pins 521 within the raised structure 522 are in contact with the contact points 512 within the groove 511. The shape of the raised structure 522 is approximately the same as the shape of the groove 511, and the size of the raised structure 522 is slightly smaller than the size of the groove 511, which allows the raised structure 522 to be embedded in the groove 511 in a mating, realizing the connection between the mother base 510 and the sub-base 520. In some embodiments, a side of the second adapter board 514 having the contact points 512 extends through the mounting port 513 to an outer side of the mother base 510. The shape of the recessed portion 523 within the raised structure 522 is approximately the same as the shape of the groove 511, and the size of the second adapter board 514 is slightly smaller than the size of the recessed portion 523, so that the second adapter board 514 may be embedded in the recessed portion 523 and be mated with the recessed portion 523. The double mating formed together with the raised structure 522 and the recessed portion 511 may realize the initial stabilization of the fit of the sub-base 520 to the mother base 510 and maintain a constant contact between the pop pins 521 and the contact points 512.

In some embodiments, along a protruding direction of the raised structure 522 relative to the first sub-base housing 527 in the body of the sub-base 520, an end of each of the plurality of pop pins 521 in contact with each of the plurality of the contact points 512 is lower than a side surface of the raised structure 522 away from the body of the sub-base 520. That is, the pop pins 521 are set lower than the side surface of the raised structure 522 away from the body of the sub-base 520, which may protect the pop pins 521 to avoid collision or abrasion of the pop pins 521 with external objects during movement of the sub-base 520.

In some embodiments, the transmission plug may further include a first adapter board 524, the first adapter board 524 being fixed within the mounting cavity of the sub-base 520 and covering the bottom wall of the recessed portion 523. The plurality of pop pins 521 are distributed in an array on the first adapter board 524, one end of each of the pop pins 521 may extend to the outer side of the first sub-base housing 527 through the first holes. In some embodiments, the first adapter board 524 is fixedly connected with the first sub-base housing 527. Specifically, the first adapter board 524 is provided with threaded holes, the first sub-base housing 527 is provided with a threaded post having blind hole threads on a side proximate to the first adapter board 524, and screws are sequentially passed through the first adapter board 524 and extend into the threaded post on the first sub-base housing 527, realizing the connection between the first adapter board 524 and the first sub-base housing 527.

In some embodiments, the circuit structure may also include a second circuit board 525, the transmission plug is connected with the power supply circuit 526 and the signal transmitter via the second circuit board 525, the second circuit board 525 is connected with a side of the first adapter board 524 back away from the plurality of pop pins 521, and the second circuit board 525 is fixedly connected with the second sub-base housing 528. The transmission plug is provided on the first adapter board 524, and the circuit is provided on the second circuit board 525. Such a structural setup is conducive to saving the layout space, which contributes to miniaturization of the device. In some embodiments, in order to save layout space, the second circuit board 525 overlaps with the first adapter board 524 in a projection plane perpendicular to an insertion direction of the sub-base 520 and the mother base 510.

In some embodiments, the second circuit board 525 may include one or more first snap-on interfaces 5251, the first adapter board 524 includes second snap-on interfaces 5241 corresponding to the first snap-on interfaces 5251, the first snap-on interfaces 5251 are electrically connected with the second snap-on interfaces 5241 via a flexible circuit board 529, to cause the second circuit board 525 to be electrically connected with the first adapter board 524.

In some embodiments, at least one of an indicator light (not shown in the figure), a charging port 532, a data port 533, and a button 531 may also be included on the sub-base 520 to facilitate interaction between the user and the signal acquisition device. Specifically, the color of the indicator light is used to indicate the amount of power, and may also be used to indicate whether the sub-base 520 is completely mated with the mother base 510. The charging port 532 is used in an external charging wire. The data port 533 is used in an external data wire, and the sub-base 520 transmits data with the external device via the external data wire. The button 531 is configured to toggle and control the power supply circuit on and off. In some embodiments, the sub-base 520 is provided with at least one second hole 5271 for mounting the indicator light, the charging port 532, the data port 533, or the button 531. In some embodiments, to realize a voice output within the device, the sub-base 520 may be configured to achieve an effective output of sound by opening holes, selecting materials, etc.

It should be noted that the above-described mother base 510 and sub-base 520 may be of any shape and are not limited to the rectangular structure shown in the figures. The above-described groove 511 and raised structure 522 may also be structures of any shape, without being limited to the rectangular structure shown in the figures.

In some embodiments, the sub-base 520 may be magnetically connected with the mother base 510, thereby realizing a detachable connection between the sub-base 520 and the mother base 510. In some embodiments, a first magnet 528 is located in the mounting cavity within the sub-base 520. In some embodiments, the raised structure 522 is an internally hollow structure, and an interior of the raised structure 522 is in communication with the mounting cavity of the sub-base 520, where a mounting groove for placing the first magnet is formed between a side wall corresponding to the raised structure 522 and a side wall corresponding to the recessed portion 523. Thus, when the first adapter board 524 is fixed to the first sub-base housing 527, the first adapter board 524 may fix the first magnet 528, preventing the first magnet 528 from falling off or moving. A second magnet 518 is located at the bottom wall of the groove 511 of the mother base 510 and is located at the peripheral side of the second adapter board 514. When the sub-base 520 is mated with the mother base 510, the first magnet 528 may be opposite to the second magnet 518. The first magnet 528 and the second magnet 518 may be a magnetic material, or one of the first magnet 528 and the second magnet 518 may be a magnetic material and the other may be a material capable of being magnetized by a metallic material. The first magnet 528 and the second magnet 518 may attract each other to cause the raised structure 522 to slide smoothly into the groove 511 of the mother base 510 simply by being placed near the groove 511 of the mother base 510, realizing the connection between the sub-base 520 and the mother base 510 and the electrical connection between the transmission interface and the transmission plug. In some embodiments, a plurality of first magnets 528 and a plurality of second magnets 518 may be provided to increase a magnetic suction force between the mother base 510 and the sub-base 520 to more firmly connect the mother base 510 with the sub-base 520. In some embodiments, the sub-base 520 may also be combined to realize a detachable connection with the mother base 510 through the sliding groove and the guide rail and magnetic attraction, which is conducive to maintaining a stable connection between the mother base 510 and the sub-base 520 and avoiding the relative movement of the mother base 510 and the sub-base 520 due to a violent movement of the user while wearing the signal acquisition device. After the mother base 510 is magnetically connected with the sub-base 520 through the first magnet 528 and the second magnet 518, the transmission interface is controlled to be electrically connected with the transmission plug. After disconnecting the magnetic attraction between the mother base 510 and the sub-base 520, the electrical connection pathway between the transmission interface and the transmission plug is controlled to be disconnected. That is, the magnetic connection between the first magnet 528 and the second magnet 518 may be regarded as a kind of electromagnetic switch, which may control the connecting and disconnecting of the electrical connection pathway between the mother base 510 and the sub-base 520 without setting up a physical button, which is convenient for the user to manipulate and use.

Figure 10A:
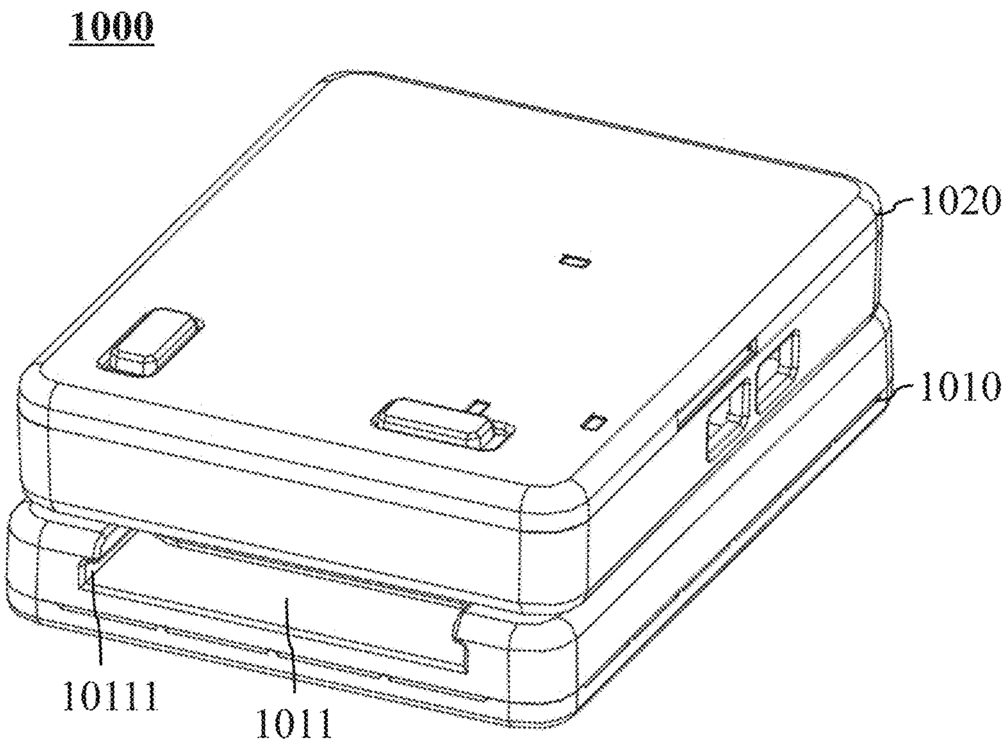
FIG. 10A is a schematic diagram illustrating a structure of a signal acquisition device according to some embodiments of the present disclosure.
Figure 10B:
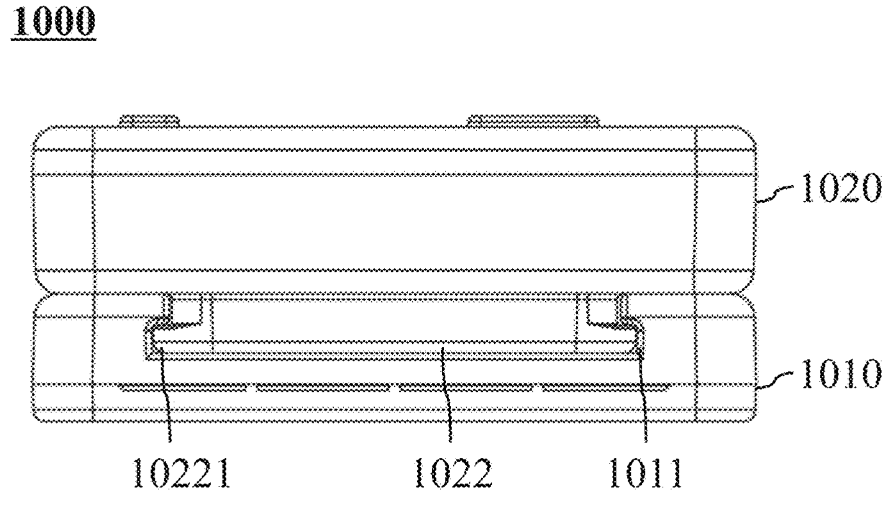
FIG. 10B is a schematic diagram illustrating another view of a structure of a signal acquisition device according to some embodiments of the present disclosure.
Figure 11:
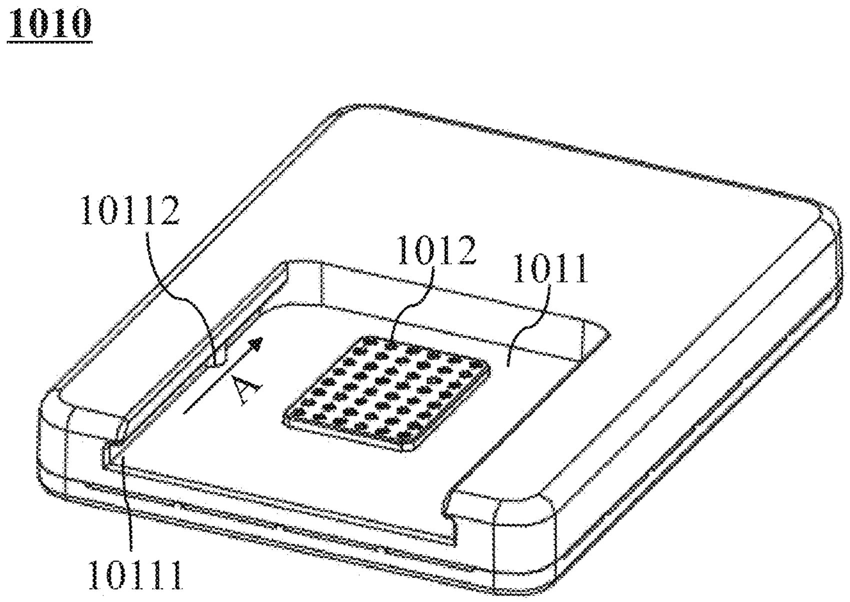
FIG. 11 is a schematic diagram illustrating a structure of a mother base according to some embodiments of the present disclosure.
Figure 12:
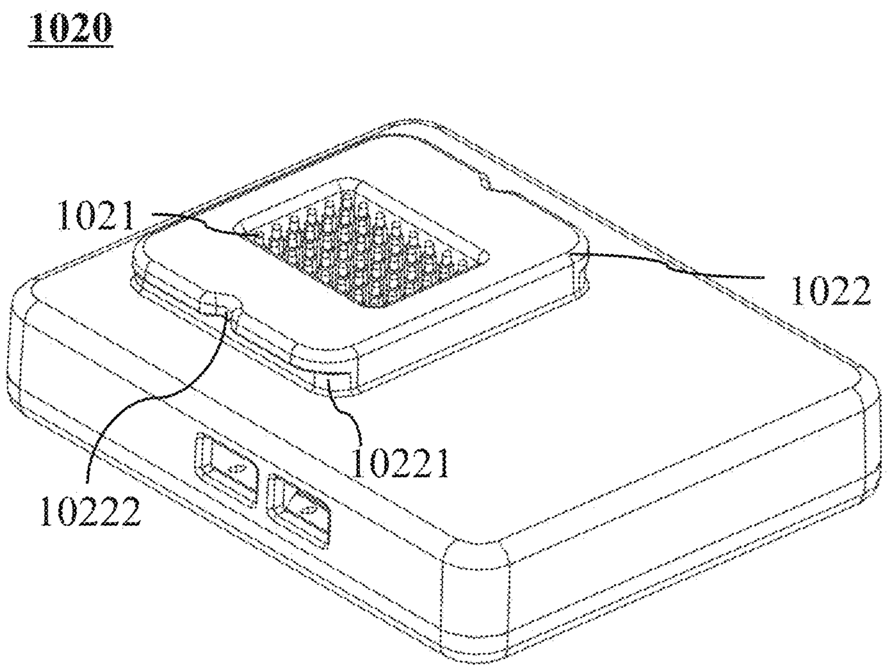
FIG. 12 is a schematic illustration illustrating a structure of a sub-base according to some embodiments of the present disclosure.

In some embodiments, the sub-base may also be detachably connected with the mother base by other means, and the detachabe connection between the sub-base and the mother base may be exemplarily illustrated in conjunction with FIG. 10A-FIG. 12 hereinafter. FIG. 10A is a schematic diagram illustrating a structure of a signal acquisition device according to some embodiments of the present disclosure. FIG. 10B is a schematic diagram illustrating another view of a structure of a signal acquisition device according to some embodiments of the present disclosure. FIG. 11 is a schematic diagram illustrating a structure of a mother base according to some embodiments of the present disclosure. FIG. 12 is a schematic illustration illustrating a structure of a sub-base according to some embodiments of the present disclosure.

As shown in FIG. 10A-FIG. 12, a signal transmission device 1000 has substantially the same overall structure as that of the signal transmission device 500 shown in FIG. 5-FIG. 9. A mother base 1010, a groove 1011, a sub-base 1020, and a raised structure 1022 shown in FIG. 10A-FIG. 12 are substantially the same as the mother base 510, the groove 511, the sub-base 511, and the raised structure 522, respectively, shown in FIG. 5-FIG. 9, and may not be repeated herein.

A main difference between the signal transmission device 1000 and the signal transmission device 500 is that a side wall of the mother base 1010 is provided with an opening, and the opening is connected with the groove 1011. In some embodiments, slide grooves 10111 are provided on two side walls of the groove 1011 adjacent to the side wall where the opening is located, and the slide grooves 10111 are recessed relative to the two side walls of the groove 1011 adjacent to the side wall where the opening is located. In some embodiments, the slide grooves 10111 extend to the side wall where the opening is located in a direction (e.g., the arrow A illustrated in FIG. 11) approximately perpendicular from the side wall where the opening is located. Guide rails 10221 mating with the slide grooves 10111 are provided on two side walls of the raised structure 1022 corresponding to two side walls of the groove 1011 adjacent to the side wall where the opening is located, and the guide rails 10221 are provided protruding from the side walls of the raised structure 1022. When the sub-base 1020 is mated with the mother base 1010, the guide rails 10221 of the sub-base 1020 may be snapped into the slide grooves 10111 of the mother base 1010, so that the guide rails 10221 slide along the slide grooves 10111 until the raised structure 1022 meets a side wall opposite the opening on the groove 1011 and stops sliding. At this time, a plurality of pop pins 1021 of the sub-base 1020 are contacted with a plurality of contact points 1012 of the mother base 1010 one by one, thereby realizing the electrical connection between a transmission interface and a transmission plug. The present embodiment realizes the detachable connection between the sub-base 1020 and the mother base 1010 through the slide grooves 10111 and the guide rails 10221 and realizes the limiting position of the sub-base 1020 during connecting with the mother base 1010, which facilitates a one-to-one connection between the plurality of pop pins 1021 and the plurality of contact points 1012.

In some embodiments, a shape of a cross-section of each guide rail 10221 along a direction perpendicular to a length direction of the guide rail 10221 may be triangular, quadrilateral, T-shaped, and other arbitrary shapes. When the raised structure 1022 is required to be embedded in the groove 1011, the guide rails 10221 may be snapped into the slide groove 10111*s* and slide relative to the slide groove 10111*s*. Positions of the guide rails 10221 and the slide grooves 10111 may be exchanged, i.e., the slide grooves 10111 are provided on the side wall of the raised structure 1022, and the guide rails are provided on a side wall of the groove 1011 corresponding to the side wall of the raised structure 1022.

In some embodiments, the signal acquisition device may further include a limit assembly, and the limit assembly may include one or more bumps 10112 and notches 10222 mating with the bumps 10112. The bumps 10112 may be inside the slide grooves 10111, and the notches 10222 may be mounted on the guide rails 10221. When the sub-base 1020 is inserted into the mother base 1010, the guide rails 10221 slide in the slide grooves 10111 along an A-direction, and the guide rails 10221 stop sliding when the raised structure 1022 resists a side wall opposite the opening on the groove 1011. The bumps 10112 cooperate with the notched 10222 to limit positions and improve a strength of the connection between the sub-base 1020 and the mother base 1010.

It should be noted that the above description of the signal acquisition device is only exemplary, and does not limit the present disclosure to the scope of the cited embodiments. It should be noted that different embodiments may produce different beneficial effects, and in different embodiments, the beneficial effects that may be produced may be any one or a combination of any one or more of the above, or any other beneficial effect that may be obtained.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements, and amendments to the present disclosure. These alterations, improvements, and amendments are intended to be suggested by this disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure, or feature described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. In addition, some features, structures, or features in the present disclosure of one or more embodiments may be appropriately combined.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes.

History application documents that are inconsistent or conflictive with the contents of the present disclosure are excluded, as well as documents (currently or subsequently appended to the present specification) limiting the broadest scope of the claims of the present disclosure. By way of example, should there be any inconsistency or conflict between the description, definition, and/or the use of a term associated with any of the incorporated material and that associated with the present document, the description, definition, and/or the use of the term in the present document shall prevail.

Finally, it should be understood that the embodiments in the present application are used only to illustrate the principles of the embodiments of the present application. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A signal acquisition device, comprising:

a wearable object provided with a sensor, wherein the wearable object is configured to be worn on a user and acquire a physiological signal of the user via the sensor;

a sub-base configured to accommodate a circuit structure, wherein the circuit structure includes a power supply circuit and a signal transmitter, the power supply circuit is configured to supply power to the sensor, and the signal transmitter is configured to send the physiological signal to an external device; and a mother base fixed on the wearable object, wherein the sub-base is detachably connected with the mother base, the mother base includes a transmission interface, and when the mother base is connected with the sub-base, the circuit structure is electrically connected with the sensor via the transmission interface;

wherein the circuit structure includes a transmission plug adapted to the transmission interface;

one of the transmission plug and the transmission interface includes a plurality of pop pins, and the plurality of pop pins are distributed in an array;

the other of the transmission plug and the transmission interface includes a plurality of contact points, and the plurality of contact points correspond to the plurality of pop pins one by one;

when the transmission plug is electrically connected with the transmission interface, end portions of the plurality of contact points are in contact with end portions of the plurality of pop pins one by one;

the mother base further includes a second circuit board, and the transmission interface is connected with a wire of the second circuit board;

the signal acquisition device includes a plurality of conducting wires; and for each of the plurality of conducting wires, one end of the conducting wire is electrically connected with the sensor, and another end of the conducting wire is connected with one contact point or one pop pin of the transmission interface through the wire of the second circuit board.

2. The signal acquisition device of claim 1, wherein the transmission plug is electrically connected with the signal transmitter and the power supply circuit; and the mother base is provided with a groove, at least a portion of the sub-base is detachably connected with the mother base through the groove, wherein:

the transmission interface is located at the groove, and the transmission plug is electrically connected with the transmission interface when the sub-base is connected with the mother base.

3. The signal acquisition device of claim 2, wherein the sub-base includes a raised structure adapted to the groove, the raised structure projects outwardly relative to a body of the sub-base, and the transmission plug is embedded in the raised structure, wherein:

the transmission plug is electrically connected with the transmission interface when the raised structure is mated with the groove.

4. The signal acquisition device of claim 3, wherein the raised structure includes a recessed portion, a first end, and a second end, wherein the first end and the second end are opposite to each other along a protruding direction of the raised structure relative to the sub-base; a part of the first end away from the body of the sub-base is recessed towards the second end close to the body of the sub-base to form the recessed portion, and the transmission plug is embedded in a bottom wall of the recessed portion and is positioned within the recessed portion.

5. The signal acquisition device of claim 4, wherein the bottom wall of the recessed portion is provided with a plurality of first holes, the plurality of first holes correspond to the plurality of pop pins one by one, and at least a portion of the plurality of pop pins protrudes through the plurality of first holes to an outer side of the sub-base.

6. The signal acquisition device of claim 5, wherein an end of each of the plurality of pop pins in contact with each of the plurality of contact points is lower than the first end of the raised structure away from the body of the sub-base along the protruding direction of the raised structure relative to the sub-base.

7. The signal acquisition device of claim 5, wherein the transmission plug further includes a first adapter board, the first adapter board is located in the sub-base and covers the bottom wall of the recessed portion, and the plurality of pop pins are distributed on the first adapter board; the sub-base includes a first sub-base housing and a second sub-base housing, the first sub-base housing and the second sub-base housing are collocated to form the body of the sub-base having a mounting cavity provided inside the sub-base, and the first adapter board is fixed within the mounting cavity of the sub-base.

8. The signal acquisition device of claim 7, wherein the circuit structure further includes a first circuit board, the transmission plug is connected with the power supply circuit and the signal transmitter through the first circuit board, the first circuit board is connected to a side of the first adapter board back from the plurality of pop pins, the first circuit board overlaps with the first adapter board in a projection plane perpendicular to an insertion direction of the sub-base and the mother base, and the first circuit board is fixedly connected with the sub-base.

9. The signal acquisition device of claim 8, wherein the circuit structure further includes a flexible circuit board, the first circuit board includes a first snap-on interface, the first adapter board includes a second snap-on interface, and two ends of the flexible circuit board are electrically connected with the first snap-on interface and the second snap-on interface, respectively, to cause the first circuit board to be electrically connected with the first adapter board.

10. The signal acquisition device of claim 1, wherein the sub-base further includes at least one of an indicator light, a charging port, a data port, and a button, the sub-base is provided with at least one second hole for mounting the indicator light, the charging port, the data port, or the button.

11. The signal acquisition device of claim 2, wherein the groove is provided with a mounting port, the mounting port is located at a bottom of the groove, and the transmission interface is embedded in the groove through the mounting port.

12. The signal acquisition device of claim 11, wherein the transmission interface further includes a second adapter board, the second adapter board is fixed inside the mounting port, the second adapter board is provided with a plurality of third holes for fixing the plurality of contact points, and a side of the second adapter board on which the plurality of contact points are provided extends to an exterior of the mother base through the mounting port.

13. The signal acquisition device of claim 12, wherein the second circuit board is connected to a side of the second adapter board back from the end portions of the plurality of contact points in contact with the plurality of pop pins to cause the plurality of contact points to be connected with the wire of the second circuit board, and the second circuit board is fixedly connected with a housing of the mother base.

14. The signal acquisition device of claim 13, wherein the second circuit board is provided with a plurality of fourth holes located on a peripheral side of the second adapter board, the wire of the second circuit board extends from the plurality of fourth holes toward the plurality of contact points, the conducting wire is fixed at the plurality of fourth holes and electrically connected with the wire of the second circuit board at the plurality of fourth holes.

15. The signal acquisition device of claim 1, wherein the sub-base includes a first magnet, the first magnet is located in the sub-base, the mother base includes a second magnet, and the second magnet is located in the mother base, wherein the first magnet and the second magnet attract each other to cause the sub-base to be connected with the mother base.

16. The signal acquisition device of claim 1, wherein the sub-base is detachably connected with the mother base by a snap.

17. The signal acquisition device of claim 3, wherein a side wall of the raised structure and a side wall of the groove corresponding to the side wall of the raised structure are provided with a matching slide groove and a matching guide rail, respectively.

18. The signal acquisition device of claim 7, wherein a first magnet is located in the mounting cavity within the sub-base;

a mounting groove for placing the first magnet is formed between a side wall corresponding to the raised structure and a side wall corresponding to the recessed portion; and the first magnet is fixed to the first adapter board.

19. The signal acquisition device of claim 3, wherein a side wall of the mother base is provided with an opening, and the opening is in communication with the groove;

slide grooves are provided on two side walls of the groove adjacent to the side wall where the opening is located, and the slide grooves are recessed relative to the two side walls of the groove adjacent to the side wall where the opening is located;

the slide grooves extend to the side wall where the opening is located in an extending direction perpendicular from the side wall where the opening is located, and the extending direction is perpendicular to an insertion direction of the sub-base to the mother base;

guide rails configured to mate with the slide grooves are provided on two side walls of the raised structure corresponding to the two side walls of the groove adjacent to the side wall where the opening is located, and the guide rails are provided protruding from the side walls of the raised structure; and when the sub-base is mated with the mother base, the guide rails of the sub-base are inserted into the slide grooves of the mother base along the extending direction, so that the guide rails slide along the slide grooves until the raised structure meets a side wall opposite to the opening on the groove and stops sliding.

20. The signal acquisition device of claim 19, further comprising a limit assembly, the limit assembly includes one or more bumps and one or more notches mating with the one or more bumps;

the one or more bumps are inside the slide grooves, and the one or more notches are mounted on the guide rails.

* * * * *